(12) United States Patent
Lan

(10) Patent No.: US 10,167,426 B2
(45) Date of Patent: Jan. 1, 2019

(54) REACTIVE PERPENDICULAR ALIGNED ORGANOSILICON MATERIAL AND MANUFACTURE METHOD OF LIQUID CRYSTAL DISPLAY PANEL

(71) Applicant: Shenzhen China Star Optoelectronics Technology Co., Ltd., Shenzhen (CN)

(72) Inventor: Song Lan, Shenzhen (CN)

(73) Assignee: SHENZHEN CHINA STAR OPTOELECTRONICS TECHNOLOGY CO., LTD., Shenzhen, Guangdong (CN)

( * ) Notice: Subject to any disclaimer, the term of this patent is extended or adjusted under 35 U.S.C. 154(b) by 391 days.

(21) Appl. No.: 14/914,646

(22) PCT Filed: Dec. 23, 2015

(86) PCT No.: PCT/CN2015/098500
§ 371 (c)(1),
(2) Date: Feb. 26, 2016

(87) PCT Pub. No.: WO2017/084147
PCT Pub. Date: May 26, 2017

(65) Prior Publication Data
US 2018/0030353 A1    Feb. 1, 2018

(30) Foreign Application Priority Data

Nov. 17, 2015    (CN) .......................... 2015 1 0797130

(51) Int. Cl.
*G02F 1/1337*    (2006.01)
*C09K 19/56*    (2006.01)
(Continued)

(52) U.S. Cl.
CPC ................ *C09K 19/56* (2013.01); *C07F 7/12* (2013.01); *C07F 7/122* (2013.01); *C09K 19/322* (2013.01);
(Continued)

(58) Field of Classification Search
CPC . C07F 7/12; C07F 7/122; C09K 19/52; C09K 19/56; C09K 2019/0448; C09K 2019/122; G02F 1/133719
(Continued)

(56) References Cited

U.S. PATENT DOCUMENTS 5,186,986 A     2/1993  Ogawa
5,468,519 A *  11/1995  Akiyama .......... G02F 1/133719
                                                            257/40
(Continued)

FOREIGN PATENT DOCUMENTS

CN    1228543 A    9/1999
CN    1234877 A    11/1999
(Continued)

*Primary Examiner* — John A McPherson
(74) *Attorney, Agent, or Firm* — Leong C. Lei (57) ABSTRACT

The disclosure provides a reactive perpendicular aligned organosilicon material and a manufacture method of a liquid crystal display panel, a general structural formula of the reactive perpendicular aligned organosilicon material is A-R, A is —SiCl$_3$; R represents a linear chained or a branched chained alkyl group with 5~20 C atoms, a CH$_2$ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group. A Cl atom in the reactive perpendicular aligned organosilicon material and —OH on a surface of the substrate without a PI film can form a hydrogen bond, leading to vertical arrangement of liquid crystal molecules.

13 Claims, 6 Drawing Sheets (51) Int. Cl.
*C07F 7/12* (2006.01)
*C09K 19/52* (2006.01)
*C09K 19/32* (2006.01)
C09K 19/04 (2006.01)
C09K 19/12 (2006.01)

(52) U.S. Cl.
CPC ........ *C09K 19/52* (2013.01); *G02F 1/133719* (2013.01); *C09K 2019/0448* (2013.01); *C09K 2019/122* (2013.01); *G02F 1/133711* (2013.01)

(58) Field of Classification Search
USPC ........................................................ 349/131
See application file for complete search history.

(56) References Cited

U.S. PATENT DOCUMENTS

| | | | | |
|---|---|---|---|---|
| 6,368,681 B1* | 4/2002 | Ogawa | .................. | B82Y 30/00 |
| | | | | 349/124 |
| 2014/0285762 A1* | 9/2014 | Noma | ............... | G02F 1/133703 |
| | | | | 349/178 |
| 2016/0152896 A1* | 6/2016 | Kwon | .................. | C09K 19/406 |
| | | | | 428/1.1 |

FOREIGN PATENT DOCUMENTS

| CN | 1246143 C | 3/2006 |
|---|---|---|
| JP | 200536094 A | 2/2005 |

\* cited by examiner

REACTIVE PERPENDICULAR ALIGNED ORGANOSILICON MATERIAL AND MANUFACTURE METHOD OF LIQUID CRYSTAL DISPLAY PANEL

FIELD OF THE DISCLOSURE

The present disclosure relates to a display technology field, and more particularly to a reactive perpendicular aligned organosilicon material and a manufacture method of a liquid crystal display panel.

BACKGROUND OF THE DISCLOSURE

With the development of the display technology, flat display devices such as a liquid crystal display (LCD) are widely employed in various consumer electronics like a mobile phone, a television, personal digital assistance, a digital camera, a laptop, a desktop computer, locating in the mainstream of display devices.

Most of liquid crystal display devices on the market are backlight liquid crystal displays, including liquid crystal display panels and backlight modules. The operational principle of a liquid crystal display panel is to dispose liquid crystal molecules on two parallel glass substrates, a number of vertical and horizontal weak currents are between the two glass substrates, which can control the liquid crystal molecules to redirect by power on/off, light from the backlight module can be refracted to show images.

A liquid crystal display panel can consist of a color filter (CF) substrate, a thin film transistor (TFT) substrate, a liquid crystal (LC) between the color filter substrate and the thin film transistor substrate, and a sealant.

A layer of thin film material is disposed on the CF substrate and the TFT substrate of a liquid crystal display respectively, mainly for aligning liquid crystal molecules, which is named an alignment film (mostly polyimide (PI) material). The main component of the alignment film is a friction alignment PI material or a light alignment PI material, however, both of which have respective flaws. First, the friction alignment PI material can cause problems like dust particles, static electricity residue, brushing streak, which can reduce yield of the product, though the light alignment PI material can avoid the problems above, heat resistance, ageing resistance and LC molecules anchorage are poor due to the property of material, affecting quality of a panel; second, PI materials have strong polarity and hygroscopicity, alignment can be inconsistent after storage and transportation, and the price of PI materials is high, a process of filming on a TFT-LCD is complicated, resulting in increasing costs of a panel. If alignment of liquid crystal molecules can be achieved without a PI film, costs of a panel can be reduced significantly.

SUMMARY OF THE DISCLOSURE

The objective of the present disclosure is to provide a reactive perpendicular aligned organosilicon material, a Cl atom in the reactive perpendicular aligned organosilicon material and —OH on a surface of the substrate without a PI film can form a hydrogen bond during heating, leading to vertical arrangement of liquid crystal molecules; —Si—Cl in the organosilicon material and —OH on the surface of the substrate react to form a —Si—O— bond, which can anchor the reactive perpendicular aligned organosilicon material on the surface of the substrate by means of a chemical bond, in order to improve stability of anchored liquid crystal molecules.

The present disclosure further provides a manufacture method of a liquid crystal display panel, compared with conventional technology, a process of a PI film can be glossed over, which can reduce costs for production and boost productivity, and alignment of liquid crystal molecules is good in effect.

The disclosure provides a reactive perpendicular aligned organosilicon material to chase the purpose above, whose general structural formula is A-R, A is —SiCl$_3$; R represents a linear chained or a branched chained alkyl group with 5~20 C atoms, a CH$_2$ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group.

A structural formula of the reactive perpendicular aligned organosilicon material is:

The disclosure further provides a manufacture method for a liquid crystal display panel, including following steps:

step 1, providing a CF substrate, a TFT substrate, and a liquid crystal mixture; a first electrode is disposed on a surface of a side of the CF substrate, a second electrode is disposed on a surface of a side of the TFT substrate; the liquid crystal mixture includes liquid crystal molecules, reactive perpendicular aligned organosilicon materials, and reactive monomers; a general structural formula of the reactive perpendicular aligned organosilicon material is A-R, A is —SiCl$_3$; R represents a linear chained or a branched chained alkyl group with 5~20 C atoms, a CH$_2$ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group; dropping the liquid crystal mixture on a surface of a side of the TFT substrate whereon the second electrode disposed by a liquid crystal dropping process, gluing frame adhesive on margins of a surface of a side of the CF substrate whereon the first electrode disposed, pasting the CF substrate and the TFT substrate in vacuum; meanwhile, a Cl atom in the reactive perpendicular aligned organosilicon material and —OH on a surface of the substrate forming a hydrogen bond, leading to array perpendicularly on the substrate, in order to make liquid crystal molecules be perpendicular to the CF substrate and the TFT substrate;

step 2, UV radiating for solidification and heating for solidification of the frame adhesive, in the process of heating for solidification of the frame adhesive, —Si—Cl in the reactive perpendicular aligned organosilicon material and —OH on surfaces of the CF substrate and the TFT substrate reacting, removing HCl to form a —Si—O— bond, which can anchor the reactive perpendicular aligned organosilicon material on surfaces of the CF substrate and the TFT substrate by means of a —Si—O— bond;

step 3, applying voltage to two sides of the liquid crystal mixture by the first electrode and the second electrode, redirecting liquid crystal molecules;

step 4, applying voltage to two sides of the liquid crystal mixture and simultaneously radiating UV light on the liquid crystal mixture to polymerize the reactive perpendicular aligned organosilicon materials and the reactive monomers on surfaces of the CF substrate and the TFT substrate, in order to anchor liquid crystal molecules;

step 5, removing voltage from the two sides of the liquid crystal mixture, making liquid crystal molecules to engender a pre-tilt angle.

A structural formula of the reactive perpendicular aligned organosilicon material is:

The reactive monomer is one or more of following four compounds:

In the liquid crystal mixture, content of the reactive perpendicular aligned organosilicon materials is 0.1%~5 wt %; content of the reactive monomers is 0.01~0.1 wt %.

The first electrode and the second electrode are a common electrode and a pixel electrode respectively.

In the step 2, the frame adhesive is radiated to solidify by a UV light with illumination of 65 mW/cm$^2$, a temperature of the solidification process with high temperature of the frame adhesive is 120° C.

In the step 3 and step 4, a value of the voltage applied to the two sides of the liquid crystal mixture is 15~25V.

In the step 4, intensity of the UV light radiated on the liquid crystal display panel is 50~85 mW/cm$^2$; a wavelength of the UV light is 365 nm.

The disclosure further provides a manufacture method of a liquid crystal display panel, including following steps:

step 1, providing a CF substrate, a TFT substrate, and a liquid crystal mixture; a first electrode is disposed on a surface of a side of the CF substrate, a second electrode is disposed on a surface of a side of the TFT substrate; the liquid crystal mixture includes liquid crystal molecules, reactive perpendicular aligned organosilicon materials, and reactive monomers; a general structural formula of the reactive perpendicular aligned organosilicon material is A-R, A is —SiCl$_3$; R represents a linear chained or a branched chained alkyl group with 5~20 C atoms, a CH$_2$ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group; dropping the liquid crystal mixture on a surface of a side of the TFT substrate whereon the second electrode disposed by a liquid crystal dropping process, gluing coat frame adhesive on margins of a surface of a side of the CF substrate whereon the first electrode disposed, pasting the CF substrate and the TFT substrate in vacuum; meanwhile, a Cl atom in the reactive perpendicular aligned organosilicon material and —OH on a surface of the substrate forming a hydrogen bond, leading to array perpendicularly on the substrate, in order to make liquid crystal molecules be perpendicular to the CF substrate and the TFT substrate;

step 2, UV radiating for solidification and heating for solidification of the frame adhesive, in the process of heating for solidification of the frame adhesive, —Si—Cl in the reactive perpendicular aligned organosilicon material and —OH on surfaces of the CF substrate and the TFT substrate reacting, removing HCl to form —Si—O— bond, which can anchor the reactive perpendicular aligned organosilicon material on surfaces of the CF substrate and the TFT substrate by means of —Si—O— bond;

step 3, applying voltage to two sides of the liquid crystal mixture by the first electrode and the second electrode, redirecting liquid crystal molecules;

step 4, applying voltage to two sides of the liquid crystal mixture and simultaneously radiating UV light on the liquid crystal mixture to polymerize the reactive perpendicular aligned organosilicon materials and the reactive monomers on surfaces of the CF substrate and the TFT substrate, in order to anchor liquid crystal molecules;

step 5, removing voltage from the two sides of the liquid crystal mixture, making liquid crystal molecules to engender a pre-tilt angle;

in the step 2, the frame adhesive is radiated to solidification by a UV light with illumination of 65 mW/cm², a temperature of the solidification process with high temperature of the frame adhesive is 120° C.; in the step 3 and step 4, a value of the voltage applied to the two sides of the liquid crystal mixture is 15~25V; in the step 4, intensity of the UV light radiated on the liquid crystal display panel is 50~85 mW/cm²; a wavelength of the UV light is 365 nm.

Advantages of the disclosure: the disclosure provides a reactive perpendicular aligned organosilicon material and a manufacture method of a liquid crystal display panel, a general structural formula of the reactive perpendicular aligned organosilicon material is A-R, A is —SiCl₃; R represents a linear chained or a branched chained alkyl group with 5~20 C atoms, a CH₂ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group. a Cl atom in the reactive perpendicular aligned organosilicon material and —OH on a surface of the substrate without a PI film can form a hydrogen bond, leading to vertical arrangement of liquid crystal molecules; —Si—Cl in the organosilicon material and —OH on the surface of the substrate react to form a —Si—O— bond during heating, which can anchor the reactive perpendicular aligned organosilicon material on the surface of the substrate by means of a chemical bond, in order to improve stability of anchored liquid crystal molecules; a liquid crystal display panel adopting the reactive perpendicular aligned organosilicon material can be without an alignment film, which can simplify the process of a TFT-LCD as well as reducing costs of producing a TFT-LCD significantly; the method for aligning liquid crystals is easily processed, a process of a PI film can be glossed over, which can reduce costs for production and boost productivity, and alignment of liquid crystal molecules is good in effect.

In order to more clearly illustrate the embodiments of the present disclosure, detailed description and figures relevant to the disclosure can be referred, it is obvious that the drawings are merely for reference and embodiments instead of limiting the disclosure.

BRIEF DESCRIPTION OF THE DRAWINGS

Embodiments of the disclosure will be described in detail and illustrated by figures to clarify the proposal and the advantages of the disclosure.

In figures.

DETAILED DESCRIPTION OF PREFERRED EMBODIMENTS

Embodiments of the present disclosure are described in detail with the accompanying drawings to illustrate the proposal and performance as follows.

Figure 1:
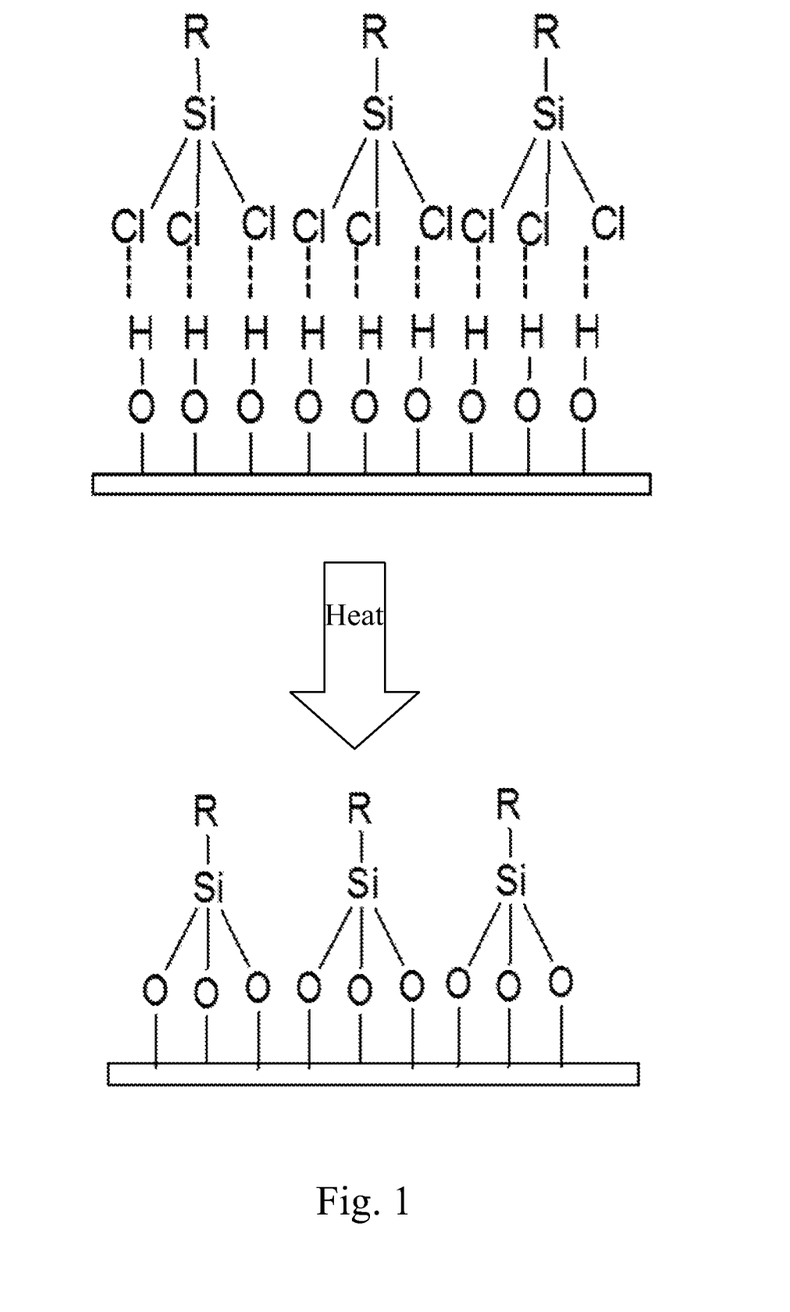
FIG. 1 is a diagram of reaction of a reactive perpendicular aligned organosilicon materials and a surface of a substrate of the present disclosure.

Referring to FIG. 1, the disclosure provides a reactive perpendicular aligned organosilicon material, whose general structural formula is A-R, A is —SiCl₃; R represents a linear chained or a branched chained alkyl group with 5~20 C atoms, a CH₂ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group.

Preferably, a structural formula of the reactive perpendicular aligned organosilicon material is:

As shown in FIG. 1, the reactive perpendicular aligned organosilicon material of the disclosure mainly includes two components—a head group A an end group R, the primary function of the head group A is to form a hydrogen bond with —Cl and —OH on a surface of the substrate, leading to the reactive perpendicular aligned organosilicon materials array perpendicularly on the substrate by hydrogen bonds, —Si—Cl in the head group A and —OH on the surface of the substrate react to form a —Si—O— bond during heating, which can anchor the reactive perpendicular aligned organosilicon material on the surface of the substrate by chemical bonds, in order to improve stability of anchored liquid crystal molecules, the primary function of the end group R is similar to that of a polyimide branch, which is vertically aligning liquid crystal molecules by stereo obstacle.

Two embodiments are employed to illustrate a preparation method of the reactive perpendicular aligned organosilicon material of the disclosure:

Embodiment 1 (a Reactive Perpendicular Aligned Organosilicon Material Synthesized with Aromatic Amines)

step 1, measuring aromatic amine (I), HCl, NaNO$_2$ with a mole ratio of 1:(1~5):(1.01~1.10), placing the measured aromatic amines (I), hydrochloric acid, and NaNO$_2$ in a reactor and stirring at 0~5° C. for 3~5 hours, obtaining a product diazo salt (II);

step 2, adding CuCl$_2$ into the diazo salt (II) produced in the step 1 with a mole ratio of CuCl$_2$:diazo salt (II)=1:1.2, and reacting at 50~100° C. for 1~5 hours; obtaining a product chlorobenzene (III);

step 3, measuring a phenyl Grignard reagent (prepared by chlorobenzene (III), Mg and LiCl) and trichlorosilane with a mole ratio of chlorobenzene (III):trichlorosilane=1:1, dissolving the measured phenyl Grignard reagent and trichlorosilane in a solvent (methylbenzene or n-hexane), employing a small amount of metal Pd as a catalyst, reacting at 130~135° C. for 1~3 hours, purified to obtain the compound (IV).

The produced compound (IV) is analyzed by H$^1$-NMR, nuclear magnetic resonance data obtained is: δ=0.96 (3H), δ=1.33 (2H), δ=1.29 (6H), δ=1.62 (2H), δ=2.55 (2H), δ=7.1 (2H), δ=7.2 (2H).

Embodiment 2 (a Reactive Perpendicular Aligned Organosilicon Material Synthesized with Aromatic Nitrile)

step 1, measuring aromatic nitrile (V) and LiAlH$_4$ with a mole ratio of 1:(1~3), measuring ether with a ratio of aromatic nitrile (V):ether=1:3 (unit ratio is mol:L), dissolving measured aromatic nitrile (V) and LiAlH$_4$ in ether; reacting at 72° C. by heating and refluxing for 1~5 hours, then adding ice water solution including 20 wt % sodium hydroxide with a volume ratio of V(NaOH)/V(ether)=2/1 in the reaction, obtaining a product aromatic amine (VI);

step 2, measuring aromatic amine (VI) produced in the step 1 above, HCl and NaNO$_2$ with a mole ratio of 1:(1~5):(1.01:1.10), placing the measured aromatic amine (VI), hydrochloric acid and NaNO$_2$ in a reactor, stirring at 0~5° C. for 3~5 hours, obtaining a product diazo salt (VII);

step 3, adding CuCl$_2$ into the diazo salt (VII) produced in the step 2 with a mole ratio of CuCl$_2$:diazo salt (II)=1:1.2, reacting at 50~100° C. for 1~5 hours; obtaining a product chlorobenzene (VIII);

step 4, measuring a phenyl Grignard reagent (prepared by chlorobenzene (VIII), Mg and LiCl) and trichlorosilane with a mole ratio of chlorobenzene (VIII):trichlorosilane=1:1, dissolving the measured phenyl Grignard reagent and trichlorosilane in a solvent (methylbenzene or n-hexane), employing a small amount of metal Pd as a catalyst, reacting at 130~135° C. for 1~3 hours, purified to obtain the compound (IX).

IX

The produced compound (IX) is analyzed by H¹-NMR, nuclear magnetic resonance data obtained is: δ=0.96(3H), δ=1.33(2H), δ=1.29(2H), δ=1.62(2H), δ=2.55(2H), δ=7.18 (2H), δ=7.43(2H), δ=7.54(4H), δ=7.5(2H), δ=7.3(2H).

The disclosure provides a reactive perpendicular aligned organosilicon material, a Cl atom in the reactive perpendicular aligned organosilicon material and a —OH on a surface of the substrate without a PI film can form a hydrogen bond, leading to vertical arrangement of liquid crystal molecules; —Si—Cl in the organosilicon material and —OH on the surface of the substrate react to form a —Si—O— bond during heating, which can anchor the reactive perpendicular aligned organosilicon material on the surface of the substrate by means of a chemical bond, in order to improve stability of anchored liquid crystal molecules; a liquid crystal display panel adopting the reactive perpendicular aligned organosilicon material can be without an alignment film, which can simplify the process of a TFT-LCD as well as reducing costs of producing a TFT-LCD significantly.

Figure 2:
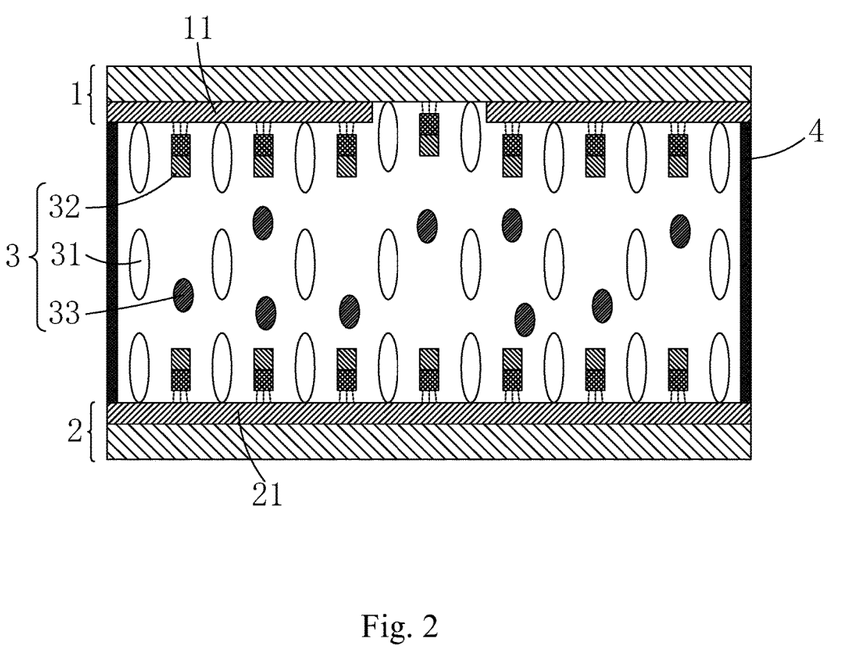
FIG. 2 is a diagram of step 1 of a manufacture method of a liquid crystal display panel of the disclosure.

Referring to FIGS. 2-5, the disclosure further provides a manufacture method of a liquid crystal display panel based on the reactive perpendicular aligned organosilicon material above, including following steps:

step 1, as shown in FIG. 2, providing a CF substrate 1, a TFT substrate 2 and a liquid crystal mixture 3; a first electrode 11 is disposed on a surface of a side of the CF substrate 1, a second electrode 21 is disposed on a surface of a side of the TFT substrate 2; the liquid crystal mixture 3 includes liquid crystal molecules 31, reactive perpendicular aligned organosilicon materials 32, and reactive monomers 33; a general structural formula of the reactive perpendicular aligned organosilicon material is A-R, A is —SiCl₃; R represents a linear chained or a branched chained alkyl group with 5~20 C atoms, a CH₂ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group; dropping the liquid crystal mixture 3 on a surface of a side of the TFT substrate 2 whereon the second electrode 21 disposed by a liquid crystal dropping process, gluing frame adhesive 4 on margins of a surface of a side of the CF substrate 1 whereon the first electrode 11 disposed, pasting the CF substrate 1 and the TFT substrate 2 in vacuum; meanwhile, a Cl atom in the reactive perpendicular aligned organosilicon material 32 and —OH on a surface of the substrate form a hydrogen bond, leading to array perpendicularly on the substrate, in order to make liquid crystal molecules 31 be perpendicular to the CF substrate 1 and the TFT substrate 2.

Preferably, a structural formula of the reactive perpendicular aligned organosilicon material 32 is:

Specifically, the reactive monomer 33 can be any reactive monomer in polymer stabilized vertically aligned (PSVA) technology.

Preferably, the reactive monomer 33 can be one or more of following four compounds:

Preferably, in the liquid crystal layer 3, content of the reactive perpendicular aligned organosilicon materials 32 is 0.1%~5 wt %; content of the reactive monomers 33 is 0.01~0.1 wt %.

Specifically, the first electrode 11 and the second electrode 21 are a common electrode and a pixel electrode respectively.

Figure 3:
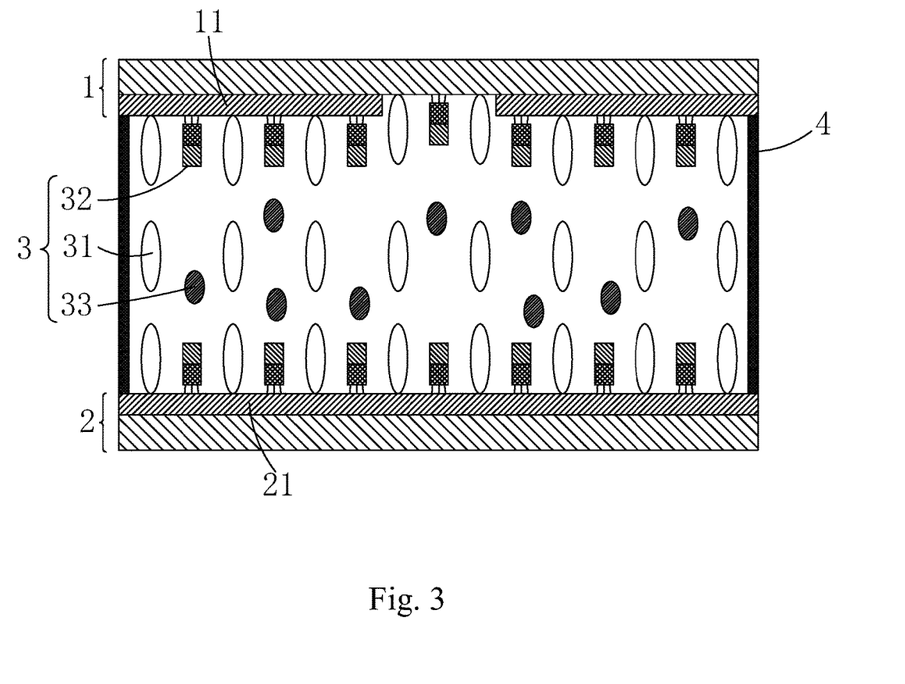
FIG. 3 is a diagram of step 2 of a manufacture method of a liquid crystal display panel of the disclosure.

Step 2, as shown in FIG. 3, radiating the frame adhesive 4 by a UV light with intensity of 65 mW/cm² for solidification, then heating it at 120° C. for solidification, during the process of heating for solidification of the frame adhesive 4, —Si—Cl in the reactive perpendicular aligned organosilicon material 32 and —OH on surfaces of the CF substrate 1 and the TFT substrate 2 react, removing HCl to form a —Si—O— bond, which can anchor the reactive perpendicular aligned organosilicon material 32 on surfaces of the CF substrate 1 and the TFT substrate 2 by means of a —Si—O— bond.

Figure 4:
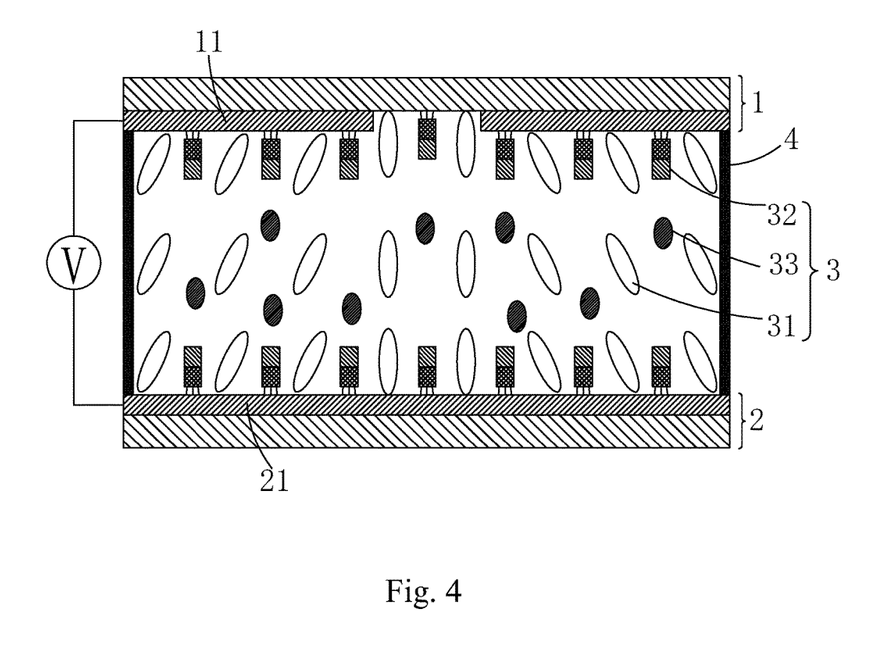
FIG. 4 is a diagram of step 3 of a manufacture method of a liquid crystal display panel of the disclosure.

Step 3, as shown in FIG. 4, applying a voltage of 15~25V to two sides of the liquid crystal layer 3 by the first electrode 11 and the second electrode 21 to redirect liquid crystal molecules 31.

Figure 5:
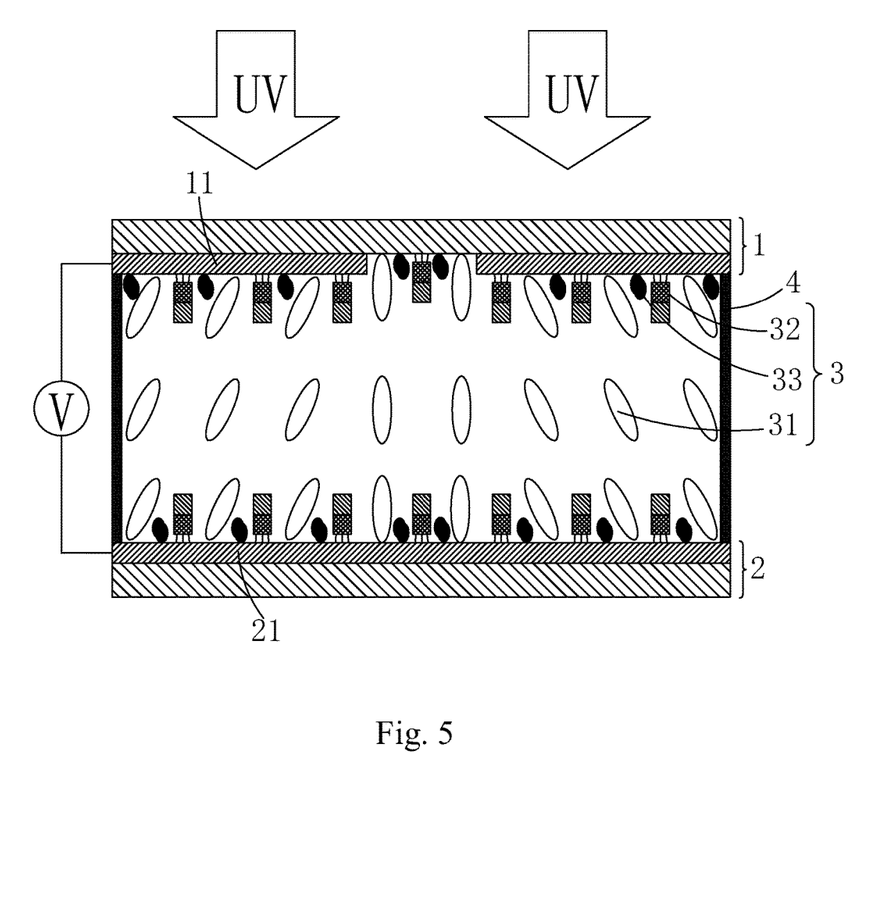
FIG. 5 is a diagram of step 4 of a manufacture method of a liquid crystal display panel of the disclosure.

Step 4, as shown in FIG. 5, applying the voltage of 15~25V to two sides of the liquid crystal mixture 3 and simultaneously radiating UV light with intensity of 50~85 mW/cm$^2$ on the liquid crystal mixture 3, polymerizing the reactive perpendicular aligned organosilicon materials 32 and the reactive monomers 33 on the first substrate 1 and the second substrate 2 to anchor liquid crystal molecules 31.

Preferably, a wavelength of the UV light is 365 nm.

Figure 6:
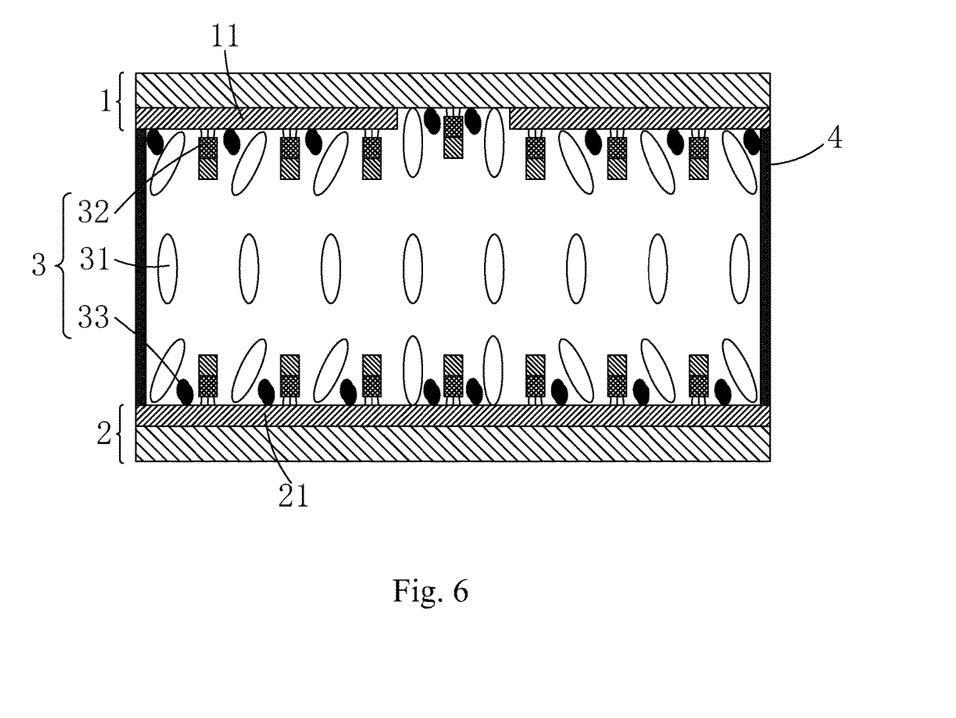
FIG. 6 is a diagram of step 5 of a manufacture method of a liquid crystal display panel of the disclosure.

Step 5, as shown in FIG. 6, removing voltage from the two sides of the liquid crystal layer 3, making liquid crystal molecules 31 to engender a pre-tilt angle.

The disclosure provides a manufacture method of a liquid crystal display panel, which disposes a liquid crystal mixture between a CF substrate without a PI film and a TFT substrate, the liquid crystal mixture includes liquid crystal molecules, reactive perpendicular aligned organosilicon materials, and reactive monomers, —Si—Cl in the reactive perpendicular aligned organosilicon material and —OH on a surface of the substrate react to form —Si—O— bond, which is anchored on a surface of a substrate by chemical bonds, leading to liquid crystal molecules array perpendicularly to the CF substrate and the TFT substrate, then the liquid crystal mixture is loaded with a voltage to redirect liquid crystal molecules, the liquid crystal mixture is finally radiated by a UV light, in order to polymerize reactive perpendicular aligned organosilicon materials and reactive monomers on the CF substrate and the TFT substrate for anchoring liquid crystal molecules, after removing the voltage, liquid crystal molecules engender a pre-tilt angle. Compared with conventional technology, the manufacture method of a liquid crystal display panel of the disclosure can be processed easily, a PI film can be glossed over, which is able to reduce costs for production and boost productivity, and alignment of liquid crystal molecules is good in effect.

Overall, the disclosure provides a reactive perpendicular aligned organosilicon material and a manufacture method of a liquid crystal display panel, a general structural formula of the reactive perpendicular aligned organosilicon material is A-R, A is —SiCl$_3$; R represents a linear chained or a branched chained alkyl group with 5~20 C atoms, a CH$_2$ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group. A Cl atom in the reactive perpendicular aligned organosilicon material and —OH on a surface of the substrate without a PI film can form a hydrogen bond, leading to vertical arrangement of liquid crystal molecules; —Si—Cl in the organosilicon material and —OH on the surface of the substrate react to form a —Si—O— bond during heating, which can anchor the reactive perpendicular aligned organosilicon material on the surface of the substrate by means of a chemical bond, in order to improve stability of anchored liquid crystal molecules; a liquid crystal display panel adopting the reactive perpendicular aligned organosilicon material can be without an alignment film, which can simplify the process of a TFT-LCD as well as reducing costs of producing a TFT-LCD significantly; the method for aligning liquid crystals is easily processed, a process of a PI film can be glossed over, which can reduce costs for production and boost productivity, and alignment of liquid crystal molecules is good in effect.

It is understandable in practical to a person skilled in the art that all or portion of the processes in the method according to the aforesaid embodiment can be accomplished with modifications and equivalent replacements, which should be covered by the protected scope of the disclosure.

What is claimed is:

1. A manufacture method of a liquid crystal display panel, comprising following steps:
    step 1, providing a CF substrate, a TFT substrate, and a liquid crystal mixture;
    wherein a first electrode is disposed on a surface of a side of the CF substrate, a second electrode is disposed on a surface of a side of the TFT substrate;
    the liquid crystal mixture comprising liquid crystal molecules, reactive perpendicular aligned organosilicon materials, and reactive monomers, wherein a general structural formula of the reactive perpendicular aligned organosilicon material is A-R, A is —SiCl$_3$; R represents a linear chained or a branched chained alkyl group with 5~20 C atoms, a CH$_2$ group in the alkyl group is substituted by a phenyl group, a naphthenic base, —CONH—, —COO—, —O—CO—, —S—, —CO— or —CH=CH—, or a F atom or a Cl atom substitutes for a H atom in the alkyl group;
    dropping the liquid crystal mixture on a surface of a side of the TFT substrate whereon the second electrode disposed by a liquid crystal dropping process, gluing frame adhesive on margins of a surface of a side of the CF substrate whereon the first electrode disposed, pasting the CF substrate and the TFT substrate in vacuum;
    meanwhile, a Cl atom in the reactive perpendicular aligned organosilicon material and —OH on a surface of the substrate forming a hydrogen bond, leading to array perpendicularly on the substrate, in order to make liquid crystal molecules be perpendicular to the CF substrate and the TFT substrate;
    step 2, UV radiating for solidification and heating for solidification of the frame adhesive, in the process of heating for solidification of the frame adhesive, —Si—Cl in the reactive perpendicular aligned organosilicon material and —OH on surfaces of the CF substrate and the TFT substrate reacting, removing HCl to form a —Si—O— bond, which can anchor the reactive perpendicular aligned organosilicon material on surfaces of the CF substrate and the TFT substrate by means of a —Si—O— bond;
    step 3, applying voltage to two sides of the liquid crystal mixture by the first electrode and the second electrode, redirecting liquid crystal molecules;
    step 4, applying voltage to two sides of the liquid crystal mixture and simultaneously radiating UV light on the liquid crystal mixture to polymerize the reactive perpendicular aligned organosilicon materials and the reactive monomers on surfaces of the CF substrate and the TFT substrate, in order to anchor liquid crystal molecules;
    step 5, removing voltage from the two sides of the liquid crystal mixture, making liquid crystal molecules to engender a pre—tilt angle.

2. The manufacture method of a liquid crystal display panel according to claim 1, wherein a structural formula of the reactive perpendicular aligned organosilicon material is:

3. The manufacture method of a liquid crystal display panel according to claim 1, wherein the reactive monomer is one or more of following four compounds:

4. The manufacture method of a liquid crystal display panel according to claim 1, wherein in the liquid crystal mixture, content of the reactive perpendicular aligned organosilicon materials is 0.1%~5 wt %; content of the reactive monomers is 0.01~0.1 wt %.

5. The manufacture method of a liquid crystal display panel according to claim 1, wherein the first electrode and the second electrode are a common electrode and a pixel electrode respectively.

6. The manufacture method of a liquid crystal display panel according to claim 1, wherein in the step 2, the frame adhesive is radiated to solidification by a UV light with illumination of 65 mW/cm$^2$, a temperature of the solidification process with high temperature of the frame adhesive is 120° C.

7. The manufacture method of a liquid crystal display panel according to claim 1, wherein in the step 3 and step 4, a value of the voltage applied to the two sides of the liquid crystal mixture is 15~25V.

8. The manufacture method of a liquid crystal display panel according to claim 1, wherein in the step 4, intensity of the UV light radiated on the liquid crystal display panel is 50~85 mW/cm$^2$; a wavelength of the UV light is 365 nm.

9. A manufacture method of a liquid crystal display panel, comprising following steps:
step 1, providing a CF substrate, a TFT substrate, and a liquid crystal mixture;
wherein a first electrode is disposed on a surface of a side of the CF substrate, a second electrode is disposed on a surface of a side of the TFT substrate;
the liquid crystal mixture comprising liquid crystal molecules, a reactive perpendicular aligned organosilicon material, and reactive monomers, wherein a general structural formula of the reactive perpendicular aligned organosilicon material is A-R, A is —SiCl$_3$; R represents a linear chained or a branched chained alkyl group with 5~20 C atoms, a CH$_2$ group in the alkyl group is substituted by a phenyl group, a naphthenic base, —CONH—, —COO—, —O—CO—, —S—, —CO— or —CH═CH—, or a F atom or a Cl atom substitutes for a H atom in the alkyl group;
dropping the liquid crystal mixture on a surface of a side of the TFT substrate whereon the second electrode disposed, gluing frame adhesive on margins of a surface of a side of the CF substrate whereon the first electrode disposed, pasting the CF substrate and the TFT substrate in vacuum;
meanwhile, a Cl atom in the reactive perpendicular aligned organosilicon material and —OH on a surface of the substrate forming a hydrogen bond, leading to array perpendicularly on the substrate, in order to making liquid crystal molecules be perpendicular to the CF substrate and the TFT substrate;
step 2, UV radiating for solidification and heating for solidification of the frame adhesive, in the process of heating for solidification of the frame adhesive, —Si—Cl in the reactive perpendicular aligned organosilicon material and —OH on surfaces of the CF substrate and the TFT substrate reacting, removing HCl to form a —Si—O— bond, which can anchor the reactive perpendicular aligned organosilicon material on surfaces of the CF substrate and the TFT substrate by means of a —Si—O— bond;
step 3, applying voltage to two sides of the liquid crystal mixture by the first electrode and the second electrode to redirect liquid crystal molecules;
step 4, applying voltage to two sides of the liquid crystal mixture and simultaneously radiating UV light on the liquid crystal mixture to polymerize the reactive perpendicular aligned organosilicon materials and the reactive monomers on surfaces of the CF substrate and the TFT substrate, in order to anchor liquid crystal molecules;

step 5, removing voltage from the two sides of the liquid crystal mixture, making liquid crystal molecules to engender a pre-tilt angle;

wherein in the step 2, the frame adhesive is radiated to solidification by a UV light with illumination of 65 mW/cm², a temperature of the solidification process with high temperature of the frame adhesive is 120° C.;

wherein in the step 3 and step 4, a value of the voltage applied to the two sides of the liquid crystal mixture is 15~25V;

wherein in the step 4, intensity of the UV light radiated on the liquid crystal display panel is 50~85 mW/cm²; a wavelength of the UV light is 365 nm.

10. The manufacture method of a liquid crystal display panel according to claim 9, wherein a structural formula of the reactive perpendicular aligned organosilicon material is:

11. The manufacture method of a liquid crystal display panel according to claim 9, wherein the reactive monomer is one or more of following four compounds:

12. The manufacture method of a liquid crystal display panel according to claim 9, wherein in the liquid crystal mixture, content of the reactive perpendicular aligned organosilicon materials is 0.1%~5 wt %; content of the reactive monomers is 0.01~0.1 wt %.

13. The manufacture method of a liquid crystal display panel according to claim 9, wherein the first electrode and the second electrode are a common electrode and a pixel electrode respectively.

* * * * *